United States Patent
Chen et al.

(10) Patent No.: US 10,085,935 B2
(45) Date of Patent: Oct. 2, 2018

(54) BEE VENOM COMPOSITION WITH EFFECTS OF PROTECTING AND BEAUTIFYING LIP

(71) Applicant: South China Sea Institute of Oceanology, Chinese Academy of Sciences, Guangdong (CN)

(72) Inventors: Hua Chen, Guangdong (CN); Huili Sun, Guangdong (CN); Si Zhang, Guangdong (CN); Jianyu Pan, Guangong (CN); Bingna Cai, Guangdong (CN); Xiaoyu Sun, Guangdong (CN)

(73) Assignee: SOUTH CHINA SEA INSTITUTE OCEANOLOGY, CHINESE ACADEMY OF SCIENCES, Guangzhou, Guangdong (CN)

( * ) Notice: Subject to any disclaimer, the term of this patent is extended or adjusted under 35 U.S.C. 154(b) by 113 days.

(21) Appl. No.: 14/650,849

(22) PCT Filed: Jan. 24, 2013

(86) PCT No.: PCT/CN2013/070952
§ 371 (c)(1),
(2) Date: Jun. 9, 2015

(87) PCT Pub. No.: WO2014/094377
PCT Pub. Date: Jun. 26, 2014

(65) Prior Publication Data
US 2015/0306025 A1    Oct. 29, 2015

(30) Foreign Application Priority Data
Dec. 20, 2012  (CN) .......................... 2012 1 0563009

(51) Int. Cl.
*A61Q 19/00* (2006.01)
*A61Q 1/00* (2006.01)
*A61Q 1/04* (2006.01)
*A61K 8/98* (2006.01)

(52) U.S. Cl.
CPC .............. *A61K 8/987* (2013.01); *A61K 8/988* (2013.01); *A61Q 1/00* (2013.01); *A61Q 1/04* (2013.01); *A61Q 19/001* (2013.01)

(58) Field of Classification Search
None
See application file for complete search history.

(56) References Cited

U.S. PATENT DOCUMENTS

| | | | | |
|---|---|---|---|---|
| 5,958,887 | A | * 9/1999 | Hansen ................. | A61K 35/63 424/230.1 |
| 2009/0041680 | A1 | * 2/2009 | Tamarkin .............. | A61Q 19/08 424/45 |
| 2010/0121083 | A1 | * 5/2010 | Tsuchida ............... | A61K 31/11 549/403 |
| 2011/0195100 | A1 | * 8/2011 | Bruning .................. | A61K 8/19 424/401 |
| 2012/0128784 | A1 | 5/2012 | Han et al. | |

FOREIGN PATENT DOCUMENTS

| | | | | |
|---|---|---|---|---|
| CN | 1088215 | A | 6/1994 | |
| CN | 1268348 | A1 | 10/2000 | |
| CN | 10188514 | | * 12/2007 | |
| CN | 101088514 | | * 12/2007 | |
| CN | 101305981 | A | 11/2008 | |
| CN | 102526116 | A | 7/2012 | |
| CN | 102548564 | A | 7/2012 | |
| KR | 20100118629 | | * 11/2010 | |
| KR | 20120038699 | A | 4/2012 | |
| WO | WO 2007/114575 | A1 | 10/2007 | |
| WO | WO2010134676 | | * 11/2010 | |
| WO | WO-2010134676 | A1 | * 11/2010 | .......... A61K 9/0019 |
| WO | WO 2012/002730 | A2 | 1/2012 | |

OTHER PUBLICATIONS

Bee Venom Lip Plumper 9g × 2, http://web.archive.org/web/20150113181215/http://www.abeeco.co.nz/shop/Skincare/Bee+Venom+Lip+Plumper+9g+x+2.html.

Aotearoa—New Zeland Bee Venom Lip Balm, http://web.archive.org/web/20150113034022/http://nz-honeybeevenom.co.nz/Beevenomlipbalm.htm.

* cited by examiner

*Primary Examiner* — Leon B Lankford, Jr.
*Assistant Examiner* — Lauren K Van Buren
(74) *Attorney, Agent, or Firm* — Muncy, Geissler, Olds & Lowe, P.C.

(57) ABSTRACT

Provided herein is a bee venom composition with effects of protecting and beautifying lips, comprising cosmetic matrix components for use on lips and bee venom. The bee venom is prepared by using the following method: crude bee venom is dissolved with water, before ultrafiltrated using an ultrafiltration membrane with the molecular weight cutoff 10000 Da, and then the resulting filtrate is freeze-dried to obtain the bee venom.

5 Claims, No Drawings

BEE VENOM COMPOSITION WITH EFFECTS OF PROTECTING AND BEAUTIFYING LIP

FIELD OF THE INVENTION

The present invention belongs to the field of cosmetics. Specifically, it relates to a bee venom composition with the effects of protecting and beautifying lips.

BACKGROUND OF THE INVENTION

Lips play a vital role in facial beauty, in addition to the function of eating, talking and smiling. The majority of people have thin lips with fuzzy lip lines and dim lip color. In order to have moisturized, sexy and plump lips, many people are attentive to personal appearance undertake lip augmentation surgery, which is very expensive, tormenting due to its side effect or adverse drug reaction. In the meantime, as the only mucosal tissue of the entire body that is always exposed to the air, lips are ⅓ of the thickness of the body skin. They are very fragile, tender and very sensitive to the outside environment. They have no sweat gland or sebaceous gland, cannot secrete grease by themselves and therefore lack a natural protective membrane. In dry and windy environment, lips will lose water easily and become dry, chapped and even desquamated. Lips have no pigment and are easily hurt by ultraviolet rays and become dim. With the increase of age, collagens in the cuticle of the lip skin decrease gradually, therefore the skin becomes lax, more and deeper lip wrinkles appear. Moreover, with poor living habits, weak physique, incomplete makeup removal and use of poor quality lip balm, the lips are easy to be inflamed and even suffer malignant lesions which induce skin cancer. Therefore, lip care cannot be ignored.

Different from skin of the other parts of the body, lips need a product with a long moisturizing effect so as to moisturize the skin of the lips and make the lips plump. At present, there are various kinds of lip care products in the market. However, a great part of them belong to the moistening or cosmetic products such as lip balm, lipstick and lip stain. Few of them have the effect of beautifying lips such as sun blocking, repairing, lip wrinkle eliminating or lip plumping. Meanwhile, those products can only temporarily remit dryness of lips or serve as the makeup. After they are removed, the condition of lip skin is not improved at all. On the contrary, the lip skin contacting allergen ingredients such as vaseline, mineral oil, chemical synthetic grease, paraffin, earth wax, colorants and essence will get dependent and allergic easily, and therefore the malaise of the lips will be increased. Therefore, it is urgent in need to develop lip protecting and beautifying products which is safe, gentle, long lasting, cheilitis preventing and appearance improving.

SUMMARY OF THE INVENTION

The objective of the present invention is to provide a safer and more efficient bee venom composition with the effects of protecting and beautifying lips, which can effectively relieve the symptoms of lip dryness, chap and desquamation, has effects of moisture retaining, nourishing, sun blocking, repairing, lip plumping and lip wrinkle eliminating, and can comprehensively enhance the lip skin's capability to resist the outside environment. It overcomes the problem that the present lip care products have no obvious effect such as improving lip dryness, desquamation or chap, which will result in dependence and allergy of skin or even more discomfort of lips, etc.

The bee venom composition with effects of protecting and beautifying lips according to the present invention comprises matrix ingredients for lip care products, characterized by also comprising bee venom.

Preferably, the bee venom is prepared by the following method: crude bee venom is dissolved with water, followed by ultrafiltration using a membrane with a molecular weight cutoff (MWCO) 10000 Da, and the filtrate is then freeze-dried to obtain the bee venom.

This present method of bee venom purification simplifies the bee venom purification process, saves costs and can effectively collect and concentrate the active substances with the effects of beautifying and skin-caring, such as melittin and apamin. Due to the removal of substances which may cause an allergic reaction, inflammation and pain to the skin, such as hyaluronidase and phospholipase $A_2$, the method remarkably enhances the effects of protecting and beautifying lips while at the same time, ensuring product safety and preventing irritation and allergy. The purification method solves the problem that the active substances with the effects of beautifying and skin-caring are ineffectively enriched in the prior art, and fills in the gap of the bee venom's application in cosmetics protecting and beautifying lips.

Preferably, the aforementioned bee venom accounts for 0.00001%~2% of the total mass of the bee venom composition.

Preferably, the bee venom is prepared by the following method: crude bee venom is completely dissolved with 10-30 times volume of water, followed by centrifugation at 5,000-10,000 g for 10-30 min; the supernatant is ultrafiltered using a membrane with a MWCO of 10,000 Da, and the filtrate is then frozen and dried to obtain the bee venom.

Preferably, the bee venom composition with the effects of protecting and beautifying lips further comprises moisturizing ingredient(s) which account(s) for 0.01%~15% of the total mass of the bee venom composition. The adding of moisturizing ingredient(s) can enhance the bee venom's effects of moisturizing, lip plumping, and lip wrinkles reducing, etc.

The moisturizing ingredient may be one or more selected from the group consisting of honey, hyaluronic acid, allantoin, aloe extract and algae extract. It can be obtained from the market, or can alternatively be prepared by the existing method.

Preferably, the bee venom composition with the effects of protecting and beautifying lips further comprises repairing ingredient(s) that account(s) for 0.01%~5% of the total mass of the bee venom composition. The adding of repairing ingredient can enhance the bee venom's effects of repairing, sun blocking, lip brightening and lip wrinkles reducing, etc.

The repairing ingredient(s) may be one or more selected from the group consisting of Vitamin E acetate, Vitamin C magnesium ascorbyl phosphate, coenzyme $Q_{10}$, olive oil and grape seed oil. It can be obtained from the market, or can alternatively be prepared by the existing method.

The crude bee venom may be crude wasp venom and/or crude honeybee venom, which can be collected by a bee venom collector or obtained from the market.

The matrix ingredients for the lip care products used in the present invention are common in this field. Those skilled in the art can select the matrix ingredients according to the various kinds of lip care products to be prepared. The matrix ingredients of lip care products can be obtained from the market.

The bee venom composition with the effects of protecting and beautifying lips according to the present invention is prepared by the following method: the bee venom in the form of powder or aqueous solution in a mass concentration of 10-50%, is homogenized or mixed together with other ingredients. The bee venom composition can be prepared by conventional processes according to the kind of the product to be prepared.

The bee venom composition with the effects of protecting and beautifying lips according to the present invention may be a lip balm, lip cream, lip gloss, lip stain or lip mask. The bee venom and the matrixes of lip care products, and the moisturizing ingredient(s) and/or repairing ingredient(s) which may optionally be further comprised, can be prepared by conventional processes to obtain the lip balm, lip cream, lip gloss, lip stain or lip mask.

The bee venom composition with the effects of protecting and beautifying lips according to the present invention has high stability, coating uniformity and good spreadability. Animal experiments and human body experiments prove that the bee venom composition with the effects of protecting and beautifying lips according to the present invention is safe. It does not induce irritation or allergy to the skin, and can effectively prevent and relieve the symptoms of lip dryness, chap and desquamation. It can comprehensively enhance the self-protection capability of the lip skin, prevent the skin from the injury of UV, brighten the lip, eliminate lip wrinkles and plump the lip.

Therefore, the bee venom composition with the effects of protecting and beautifying lips according to the present invention can be used as common lip care products or functional care products with the effects of moisturizing, nourishing, sun-blocking, repairing, lip plumping and lip wrinkle eliminating.

The present invention is developed based on the understanding of the lip tissue structure, causes and the protection method of the cheilitis, lip beautifying mechanism and the skin-caring effects of functional active ingredients, with the combination of the study findings on modern lip protecting and beautifying care products and the pharmacology. The bee venom, moisturizing ingredient(s) and repairing ingredient(s) with obvious effects of skin moisture retaining, microcirculation promoting, skin injury repairing, UV radiation resisting, inflammation eliminating, lip wrinkles reducing and lip plumping, are selected from numerous functional active ingredients, and scientifically formulated, to give a full play to the function of moisturizing, nourishing, sun-blocking, repairing, lip plumping and lip wrinkle eliminating.

The bee venom in the bee venom composition with the effects of protecting and beautifying lips according to the present invention is rich in active ingredients such as melittin, apamin, catecholamine, free amino acids, vitamins, microelements and glycerin. The molecular weights are low. It is weak in immunogenicity, does not tend to generate anaphylactic reaction, even can relieve the allergenicity of the lip care product matrixes such as the vaseline, mineral oil, chemical synthetic grease, paraffin, earth wax, colorants and flavor, to the skin.

Melittin has obvious effects of anti-oxidation and UV radiation prevention. It can eliminate inflammation and delay skin aging. It can also block the exciting conduction in the nerve synapse and weaken the flaccid paralysis and muscular tension of the lip muscles under control, so as to make the lips plump and the lip wrinkles reduced or eliminated. Apamin can enhance the capillary permeability, improve microcirculation, promote metabolism of epidermis cells and make the skin cells rejuvenate. Catecholamine has anti-inflammation effect on the skin injury by light and is good for wound healing. Active substances such as free amine acids, vitamins and microelements are helpful to the skin moisture retaining, nutrients nourishing. They are effective in anti-oxidation, tyrosinase inhibition, protection the skin from UV damage, and can comprehensively enhance the functions of the natural barrier of the skin. Glycerinum can absorb moisture in the air, prevent the skin moisture from evaporating, achieve the moistening effect and is helpful to improve the skin's self-repairing capability.

The moisturizing ingredient, honey, of the bee venom composition, is rich in nutrients, which can directly act on epidermis and dermis to provide nutrients to cells. It has moisturizing and nourishing effect, making the lip skin fine and elastic. In addition, it can recover the lip healthy and make it ruddy, reduce or eliminate lip wrinkles. Hyaluronic acid is a substance with the best moisturizing effect at present. It can seep into the corium layer, retain cellular water, prompt the proliferation of the epidermis cells and wound healing, and make the dry, chapped and desquamated lip skin to recover tenderness and smoothness. The hyaluronic acid can also prompt active ingredients such as the bee venom to be absorbed by the skin, so as to enhance the lip beautifying effect. Allantoin can promote the growth of the epithelial cells to make the epidermis to be granular quickly, providing enough water to the intercellular space when metabolizing the cutin, to make the lip skin tender and plump. The aloe extract is rich in amino acids, organic acids, polysaccharides and microelements. It can promote the active ingredients such as the bee venom to go deep into the dermis and the subcutaneous tissue, to make the lip skin smooth, soft and moist. The algae extract contains a great amount of sulfate heteropolysaccharide, which can improve the hydrature of the lip skin, reduce loss of water, re-build the natural barrier for the skin and increase the lipid granule content of the epidermal granular layer. These moisturizing ingredients and the bee venom have an obvious synergistic effect, which can obviously enhance the effects of the bee venom composition provide herein for moistening, nourishing, plumping and wrinkle reducing to the lip.

The repairing ingredient, Vitamin E acetate, in the bee venom composition of the present invention, can release free Vitamin E after seeping into the skin. Vitamin E is an important antioxidant and stabilizer in the cell membrane. It can retain the skin moisture, eliminate free radicals, inhibit lipid peroxidation, maintain the link between the elastic fibers and the collagenous tissue, accelerate cell repair and regeneration, improve lip cracking and eliminate lip wrinkles obviously. The Vitamin C magnesium ascorbyl phosphate can release free Vitamin C after seeping into the skin. As an endogenous antioxidant, Vitamin C can effectively eliminate free radicals, reduce the inflammatory response caused by UV, activate collagen metabolism, repair sunburned skin and postpone skin photoaging. In addition, Vitamin C can also enhance the stability and effectiveness of the lip care products. Coenzyme $Q_{10}$ is an effective supplement of the endogenous coenzyme Q10 in epidermis cells. It can accelerate the blood microcirculation, promote metabolism of the lip skin and proliferation of the epidermis cells, recover skin elasticity, and has obvious effects of relieving lip dimness, cracking and lip wrinkles caused by natural aging, light and diseases. Olive oil has rich squalene with very high affinity and essential fatty acids. It can be quickly absorbed by skin and maintain the elasticity and glossiness. Olive oil also contains unsaturated fatty acids, vitamins and phenols, etc., which can eliminate the lip wrinkles and prevent the skin from aging, and has obvious effects of relieving the dry and chapped symptoms of the lips. Grape seed oil contains linoleic acid, proanthocyanidin, polyunsaturated fatty acid, mineral substances, and can be very easily absorbed by skin. Grape seed oil can also help the skin to absorb Vitamin C and E, promote microcirculation, protect the collagen fibers and elastic fibers to resist UV damage, moisten the lip skin and reduce generation of the lip wrinkles. These repairing ingredients and the bee venom have an obvious synergistic effect, which can obviously enhance the effect of the bee venom composition of the present invention for sun blocking, repairing, lip brightening, and lip wrinkles reducing.

Compared with the prior art, the present invention has the following advantages:

1. Aiming at the lip skin's special physiological structure and sensitivity to the ingredients of cosmetics or skin care products, the bee venom composition with effects of protecting and beautifying lips of the present invention preferably applies pure natural bee venom as the main material. Though it is rare to add bee venom in cosmetics or skin care products, bee venom has been recorded in "Chinese version of International Nomenclature of Cosmetic Ingredients 2010" for a long time. This indicates that the application of the bee venom to cosmetics is safe and feasible. However, the problem of failure to effectively enrich the active substances with skin beautifying effect from the bee venom has not been solved yet in the prior art. In the present invention, the bee venom is purified, and the substances which cause skin allergy, inflammation and pain are effectively removed, while the melittin and apamin are highly enriched to achieve more obvious effects of protecting and beautifying lips. Moreover, the bee venom of the present invention can be quickly absorbed by skin. Meanwhile, it does not cause skin allergy and imposes no burden on skin.

2. The preferable moisturizing ingredients including honey, hyaluronic acid, allantoin, aloe extract and algae extract, etc., and the repairing ingredients including Vitamin E acetate, Vitamin C magnesium ascorbyl phosphate, coenzyme Q10, olive oil and grape seed oil, etc., of the bee venom composition with effects of protecting and beautifying lips of the present invention, are purely natural extracts. They are well compatible with lip skin and therefore can be quickly absorbed by skin. They are safe and mild, causing no irritation or allergy, imposing no burden on the skin. In addition, they can also effectively relieve the irritation effect of the lip care product matrixes to the lip skin.

3. The bee venom composition with effects of protecting and beautifying lips of the present invention can effectively supply moisture to lips, retain lips moisture, relieve the symptoms of dryness, chap and desquamation of lips, and comprehensively enhance the natural shielding function of lip skin. The bee venom composition with effects of protecting and beautifying lips of the present invention also has multi-functions of sun blocking, repairing, lip brightening, lip wrinkles reducing, and lip plumping, so as to make the lips naturally become delicate, exquisite, sanguine, shiny, plump and charming. The effects of the composition for protecting and beautifying lips are comprehensive, efficient and enduring.

4. The moisturizing ingredients such as honey, hyaluronic acid and allantoin in the bee venom composition of the present invention exhibit a notable synergistic interaction with the bee venom, so do the repairing ingredients such as Vitamin E acetate and Vitamin C magnesium ascorbyl phosphate. Thus the effects of moistening, repairing, sun blocking, lip wrinkles eliminating, lip plumping and lip brightening are enhanced, which can meet the demands of different crowds.

DETAILED DESCRIPTION OF THE EMBODIMENTS

The present invention is explained in further detail as below. However, the present invention is not limited to the embodiments provided herein. Any equivalent changes or modifications made in accordance with the present invention shall fall within the protective scope of the present invention.

The following raw materials are obtained from the market, except those specifically explained.

Embodiment 1

Crude wasp venom was collected by a bee venom collector, added with 25 times volume of water to be dissolved completely, followed by centrifugation at 8,000 g for 15 min. The supernatant was ultrafiltered using an ultra-filtration membrane with a MWCO of 10,000 Da, and the filtrate was then freeze-dried to obtain the wasp venom.

Raw materials of the wasp venom composition with the effect of lip protection and beautification in this embodiment consisted of the following ingredients, with the total weight percentage of 100%:

Phase A: 26.5% of beeswax, 5% of carnauba wax, 2% of cetanol.

Phase B: 44.5% of castor oil, 9.5% of glycerin monostearate, 4.5% of anhydrous lanolin, 2.5% of isopropyl palmitate.

Phase C: 0.00001% of wasp venom (added in powder form).

Phase D: 2% of essence, 3% of bergamot extract and 0.49999% of tertiary butylhydroquinone.

Manufacturing process: Phase A and Phase B were heated to 85° C. respectively; Phase B was then added into Phase A under agitation for well mixing. When it was cooled to 45° C., Phase C and Phase D were added, agitated and well mixed. Then the mixture was filled in a mold before abruptly cooled and demolded under vacuum. Then the surfaces were polished with mild heating to obtain the bee venom composition with effects of protecting and beautifying lips in this embodiment, which was the lip balm containing wasp venom.

The lip balm prepared in this embodiment was smooth, pore free, easy to dab and would not irritate delicate skin. After applied with the lip balm, the skin became moistened and soft, in the meantime the lip wrinkles were reduced, and the lips became plump, healthy and shiny.

Embodiment 2

Crude honeybee venom was collected by a bee venom collector, added with 10 times volume of water to be dissolved completely, followed by centrifugation at 5,000 g for 30 min. The supernatant was ultrafiltered using an ultra-filtration membrane with a MWCO of 10,000 Da, and then filtrate was freeze-dried to obtain the honeybee venom.

Raw materials of the bee venom composition with effects of protecting and beautifying lips in this embodiment consisted of the following ingredients, with the total weight percentage of 100%:

Phase A: 0.2% of Carbomer, 4% of glycerin, 3% of propylene glycol; the balance being deionized water.

Phase B: 1.5% of ceteareth-2, 2% of ceteareth-21, 3% of jojoba oil, 2% of cetearyl alcohol, 1% of glycerin monostearate, 4% of caprylic/capric triglyceride, 3% of ethylhexyl palmitate, 2% of polydimethylsiloxane, 3% of isopropyl myristate, and 0.1% of ethylparaben.

Phase C: 0.5% of crude honeybee venom (added in solution form in a mass concentration of 10% that was prepared with deionized water).

Phase D: 1% of Azone/PEG-40 hydrogenated castor oil, 0.2% of triethanolamine, 0.1% of phenoxyethanol/methylparaben/butyl hydroxybenzoate/ethylparaben/propyl hydroxybenzoate/isobutylparaben.

Manufacturing process: Phase A and Phase B were respectively heated to 80° C., Phase B was then added into Phase A under agitation for well mixing. When it was cooled to 30° C., Phase C was added into the mixture of Phase A and Phase B and mixed for 10 min. After Phase D was added, the mixture was then agitated and well mixed to obtain the bee venom composition with effects of protecting and beautifying lips in this embodiment, which was the lip cream containing honeybee venom.

The lip cream prepared in this embodiment was glossy, fine, homogeneous and had no separated oil/water phase. After dabbed to lips, the lip cream can obviously soften the surface fine lines and the deep wrinkles of lips, re-shape youthful outline, keep the lip skin moistened constantly, soften and smoothen the rough lip surface, relieve the symptoms of dryness, chap and desquamation, and make the lips natural, plump and exquisite.

Embodiment 3

Crude wasp venom was purchased from Wuhan Yimin Bee Product Company, added with 30 times volume of water to be dissolved completely, followed by centrifugation at 10,000 g for 10 min. The supernatant was ultrafiltered with an ultra-filtration membrane with a MWCO of 10,000 Da, and then filtrate was freeze-dried to obtain the wasp venom.

Crude honeybee venom was collected by a bee venom collector, added with 30 times volume of water to be dissolved completely, followed by centrifugation at 10,000 g for 10 min. The supernatant was ultrafiltered with an ultra-filtration membrane with a MWCO of 10,000 Da, and the filtrate was then freeze-dried to obtain the honeybee venom.

Raw materials of the bee venom composition with effects of protecting and beautifying lips in this embodiment consisted of the following ingredients, with the total weight percentage of 100%:

81.8% of deionized water, 0.4% of xanthan gum, 0.6% of the cross-linked polymer of acrylate/$C_{10-30}$ alkyl acrylate, 0.1% of EDTA-2Na, 5% of glycerin, 5% of propylene glycol, 5% of butanediol, 1% of wasp venom, 1% of honeybee venom (two kinds of venom were both added in powder form), and 0.1% of phenoxyethanol/methylparaben/butyl hydroxybenzoate/ethylparaben/propyl hydroxybenzoate/isobutylparaben.

Manufacturing process: The above ingredients were added in sequence, well agitated and mixed at 55° C. to obtain the bee venom composition with effects of protecting and beautifying lips in this embodiment, which was the lip gloss containing bee venom.

The lip gloss prepared in this embodiment had fine quality and was very easily absorbed by skin. After brushed with the lip gloss, the lips became moistened and plump.

Embodiment 4

Crude honeybee venom was purchased from Fujian Shenfeng Science & Technology Co., Ltd., added with 15 times volume of water to be dissolved completely, followed by centrifugation at 6,000 g for 20 min. The supernatant was ultrafiltered with an ultra-filtration membrane with a MWCO of 10,000 Da, and then the filtrate was freeze-dried to obtain the honeybee venom.

Raw materials of the bee venom composition with effects of protecting and beautifying lips in this embodiment consisted of the following ingredients, with the total weight percentage of 100%:

Phase A: 3% of calcium aluminum borosilicate, titanium dioxide, silicon dioxide (and) tin oxide.

Phase B: 61.02% of copolymer of hydrogenated polyisobutene and ethylene/propylene/styrene, 8% of ethylhexyl palmitate, 5% of glycerol tricaprylate, 3% of isooctadecyl isooctadecanoate, 0.2% of propyl p-hydroxybenzoate, 0.08% of castor oil and D&C blue NO. 27 aluminum lake, 4% of octyldodecanol PCA ester.

Phase C: 1% of PEG-40 hydrogenated castor oil, 0.5% of honeybee venom (added in solution form in a mass concentration of 10% that was prepared with distilled water), 1% of honey purchased from Yunan Baita Bee Industry Co., Ltd., 2% of hyaluronic acid purchased from the Dali Hyaluronic Acid Co., Ltd. of Liuzhou Chemical Group, and 10% of deionized water.

Phase D: 0.2% of triethanolamine, 0.5% of essence, 0.5% of phenoxyethanol/methylparaben/butyl hydroxybenzoate/ethylparaben/propyl hydroxybenzoate/isobutylparaben.

Manufacturing process: Ingredients of Phase B were mixed together, heated to 60° C. and mixed uniformly. When it was cooled to 40° C., Phase A, Phase C and Phase D which had been mixed well in advance were added into Phase B. The mixture was agitated and well mixed to obtain the bee venom composition with effects of protecting and beautifying lips in this embodiment, which was the lip stain containing honeybee venom.

The lip stain made in this embodiment had fine quality and no block. After brushed to the lips, the lip stain could immediately relieve the symptoms of dryness, chap and desquamation. The lips became moistened and plump. Lip wrinkles were relieved or eliminated. The lips recovered as natural and shaped feature.

Embodiment 5

Crude wasp venom was purchased from Wuhan Yimin Bee Product Company and then processed according to the method in the embodiment 1 to obtain the wasp venom.

Raw materials of the bee venom composition with effects of protecting and beautifying lips in this embodiment consisted of the following ingredients, with the total weight percentage of 100%:

0.00001% of wasp venom (added in solution form in a mass concentration of 10% that was prepared with deionized water), 0.01% of allantoin purchased from Wuhu Huahai Biological Engineering Co., Ltd., 1% of *macadamia ternifolia* seed oil, 1% of jojoba oil, 1% of *butyrospermum parkii* oil, 1% of coconut oil, 10% of nano pearl powder, 11% of almond powder, 1% of preservative (butylated hydroxytoluene), and the balance being deionized water.

Manufacturing process: The above ingredients were added in sequence at 30° C., then well mixed to obtain the bee venom composition with effects of protecting and beautifying lips in this embodiment, which was the lip mask containing wasp venom.

The lip mask made in this embodiment was edible directly with good taste. It could also be directly dabbed to the lips to nourish and moisten the skin. Removed and washed away the lip mask after being applied to the lips for 10-20 min, the skin became soft, moistened and plump, the wrinkles disappeared and color of the lip turned light.

Embodiment 6

Honeybee venom was made according to the method of making bee venom in embodiment 2.

Raw materials of the bee venom composition with effects of protecting and beautifying lips in this embodiment consisted of the following ingredients, with the total weight percentage of 100%:

2% of honeybee venom (added in solution form in a mass concentration of 50% that was prepared with deionized water), 1% of hyaluronic acid purchased from the Jiangsu Haihua Biotech Co., Ltd., 13% of aloe extract purchased from Xi'an Yuansen Bio-Tech Company, 1% of algae extract bought from Kunshan Zaoshanghao Gongfang Co., Ltd., 0.1% of xanthan gum, 0.5% of Carbopol Ultrez 20, 2% of glycerin, 5% of propylene glycol, 0.2% of triethanolamine, 0.1% of phenoxyethanol/methylparaben/butyl hydroxybenzoate/ethylparaben/propyl hydroxybenzoate/isobutylparaben, and the balance being water.

Manufacturing process: The above ingredients were added in sequence at 45° C., then well mixed to obtain the bee venom composition with effects of protecting and beautifying lips in this embodiment, which was the lip gloss containing the honeybee venom.

The lip gloss prepared in this embodiment had fine quality and was well absorbed by skin. After brushed to the lips, the lip gloss could immediately relieve the symptoms of dryness, chap and desquamation, moisten lips and eliminate the wrinkles. The lips recovered as plump feature.

Embodiment 7

Wasp venom was made according to the method of making bee venom in embodiment 3.

Raw materials of the bee venom composition with effects of protecting and beautifying lips in this embodiment consisted of the following ingredients, with the total weight percentage of 100%:

Phase A: 9.7% of polydimethylsiloxane, 20.1% of copolymer of polydimethylsiloxane & divinyl polydimethyl siloxane/polydimethylsiloxane.

Phase B: 14% of polyethylene.

Phase C: 2% of isohexadecane, disteardimonium hectorite (and) propylene carbonate$^{NF}$.

Phase D: 9.78% of castor oil & D&C red No. 7 aluminum lake, 0.07% of castor oil & FD&C blue No. 1 aluminum lake, 0.05% of castor oil & black iron oxide, 2.5% of triisostearyl citrate and 1% of nylon-12.

Phase E: 39.3% of cyclomethicone.

Phase F: 0.5% of wasp venom (added in solution form with a mass percentage of 50% that was prepared in deionized water), 0.5% of Vitamin E acetate bought from Zhengzhou Chengguo Commerce and Trade Co., Ltd in Henan province, and 0.5% of Vitamin C magnesium ascorbyl phosphate bought from Guangzhou Qisheng Commerce and Trade Co., Ltd.

Manufacturing process: Phase B was added into Phase A after Phase A was heated to 90° C. The mixture was agitated until completely dissolved. When it was cooled to 70-75° C., Phase C and Phase D were added respectively, and followed by homogenization. When it was cooled to 65-70° C., Phase E was added, and then mixed well. When it was cooled to 55° C., Phase F was added, and then mixed well. The mixture was poured into a mold and then cooled to obtain the bee venom composition with effects of protecting and beautifying lips in this embodiment, which was the lip stain containing wasp venom.

The lip stain made in this embodiment had fine quality, uniform spreadability and was well absorbed by skin. After applied to the lips, it could obviously brighten the lip, reshape the outline and make the lip delicate and plump.

Embodiment 8

Crude wasp venom was purchased from Wuhan Yimin Bee Product Company and then processed according to the method of making the bee venom in embodiment 2 to obtain the wasp venom.

Raw materials of the bee venom composition with effects of protecting and beautifying lips in this embodiment consisted of the following ingredients, with the total weight percentage of 100%:

Phase A: 5% of glycerin, 3% of propylene glycol, 2% of butanediol and the balance being deionized water.

Phase B: 0.00001% of wasp venom (added in powder form), 0.01% of coenzyme $Q_{10}$ purchased from ENJORE C&G (XIAMEN) BIOENGINEERING CO., Ltd. and 30% of deionized water.

Phase C: 1% of Azone/PEG-40 hydrogenated castor oil, 0.2% of triethanolamine, 0.1% of phenoxyethanol/methylparaben/butyl hydroxybenzoate/ethylparaben/propyl hydroxybenzoate/isobutylparaben.

Manufacturing process: Phase A was mixed firstly at 35° C., and then the pre-mixed Phase B was added into Phase A; Phase C was added after Phase A and Phase B were agitated and mixed well; the mixture was agitated and well mixed to obtain the bee venom composition with effects of protecting and beautifying lips in this embodiment, which was the lip mask containing wasp venom.

The lip mask made in this embodiment had no deposition, was highly transparent, easy to be absorbed with no irritation. It can be directly dabbed to the lips or soaked in a paper membrane before being applied to repair and care the lip. After applied with it, the lip desquamation and chap symptoms were obviously eliminated, and the lips became light in color with sexy and plump shape.

Embodiment 9

Honeybee venom was made according to the method of making the bee venom in embodiment 4.

Raw materials of the bee venom composition with effects of protecting and beautifying lips in this embodiment consisted of the following ingredients, with the total weight percentage of 100%:

Phase A: 12% of earth wax, 15% of bee wax, 6% of microcrystalline wax and 20% of albolene.

Phase B: 2% of olive oil bought from Northern Olive Oil Development Co., Ltd. in Guangyuan city, 2% of grape seed oil bought from Jiangsu Shan He Tang Biotechnology Co., Ltd., 10% of isopropyl myristate, 2% of lanolin fatty acid, 2% of PEG-lanolin fatty acid ester, 10% of cocoa butter and 15% of white oil.

Phase C: 2% of honeybee venom (added in powder form), 1% of Vitamin E acetate.

Phase D: 1% of essence.

Manufacturing process: The ingredients of Phase A were mixed and heated to 80° C. and then agitated well. When cooled to 60° C., Phase B which was mixed evenly in advance was added, followed by agitation for well mixing.

When the mixture was cooled to 45° C., Phase C and Phase D were added, followed by agitation for well mixing. The mixture was poured into a mold, followed by quick cooling and vacuum demolding. After the surface was baked and polished with gentle heat, the bee venom composition with effects of protecting and beautifying lips in this embodiment, which was the lip balm containing honeybee venom, was obtained.

The lip balm made in this embodiment will not cause perspiration and was easy to be applied. After applied to the lips, it can obviously repair the chapped and desquamated skin, effectively protect the skin against sunshine, make the lips turn light in color and recover to a natural and healthy state.

Embodiment 10

The bee venom compositions made in embodiments 1-9 were underwent sun-caring and repairing function tests.

Experiment objects were sample 1 (A, a), sample 2 (B, b), sample 3 (C, c), sample 4 (D, d), sample 5 (E, e), sample 6 (F, f), sample 7 (G, g), sample 8 (H, h) and sample 9 (I, i). Samples A-I were bee venom compositions made according to embodiments 1-9, successively. Samples a-i were the control groups vs. samples A-I successively, wherein the bee venom, moisturizing ingredients and repairing ingredients of samples A-I were substituted by deionized water in the same content in samples a-i; that was, samples a-i containing no bee venom, moisturizing ingredients or repairing ingredients.

54 healthy Kunming mice weighted (20±2) g, half male and half female, were randomly divided into 18 groups, each of which having 3 mice. The samples were applied on the mice for preventive purpose (each sample was applied to one group, i.e., 18 samples for 18 groups respectively). Each mouse was dabbed 0.6 mL on the back and 0.3 mL on each ear, twice a day for 4 days. The mice were horizontally fixed on iron frames and placed at a distance of 10 cm vertically away from the ultraviolet lamps to receive UV radiation for 6 h to make the mice models with damaged skin. The epidermal keratinization and chap degree of the mice were used as the evaluation indexes to describe the changes on the back skin of the mice, and the samples' effects of protecting the mice skin against UV damage were evaluated.

The mice with damaged skin were radiated for 40 h continuously before sacrificed by cervical dislocation and then weighed. The round section of two ears and the section of the back skin with a diameter of 9 mm were taken and weighed to obtain the accurate mass. Ear index (ear index=mass of ear section/mass of mouse) and skin index (skin index=mass of skin section/mass of mouse) were calculated, followed by analysis on the samples' effect on restraining the edema of mice caused by UV radiation. The back skins were taken and fixed with 10% of formaldehyde for 24 h to obtain the sealed samples. The sealed samples were placed under 10× microscope to observe the overall skin shape. Then a first picture was taken from the top of the skin observed under 40× microscope; after that, a following picture was taken when the graticule was moved every 2 mm. After 5 pictures were shot, 5 points on each picture were selected with the microscopic image analysis system to measure the surface thickness thereof. A total of 25 points were measured for each sealed sample, and the average values were recorded as the epidermis thickness to analyze the samples' effects on restraining the epidermal keratinization of the mice. Six view fields were taken from each picture, followed by calculation of the number of fibroblasts in each view field. The average value was recorded as the number of the dermal fibroblast in each view field.

The test results of ear index, skin index, epidermis thickness and fibroblast number of the UV damaged mice were shown as Table 1.

TABLE 1

Ear index, skin index, epidermis thickness and fibroblast number of the UV damaged mice

| | Sample | Ear index (mg/g) | Skin index (mg/g) | Epidermis thickness (μm) | Fibroblast number |
|---|---|---|---|---|---|
| Sample 1 | Sample A | 1.1 ± 1.0 | 3.4 ± 1.1 | 12.7 ± 3.2 | 22.1 ± 3.9 |
| | Sample a | 1.3 ± 1.1 | 3.9 ± 0.9 | 14.6 ± 2.9 | 19.1 ± 32.8 |
| Sample 2 | Sample B | 0.8 ± 0.34 | 2.4 ± 0.7 | 9.0 ± 1.9 | 30.7 ± 3.5 |
| | Sample b | 0.9 ± 0.32 | 2.8 ± 0.8 | 10.4 ± 2.6 | 26.6 ± 3.1 |
| Sample 3 | Sample C | 0.75 ± 0.25 | 2.3 ± 1.1 | 8.6 ± 1.3 | 32.4 ± 4.0 |
| | Sample c | 0.86 ± 0.27 | 2.6 ± 0.9 | 9.8 ± 2.4 | 28.2 ± 5.1 |
| Sample 4 | Sample D | 1.0 ± 0.53 | 2.9 ± 1.2 | 10.9 ± 3.8 | 25.4 ± 3.5 |
| | Sample d | 1.2 ± 0.45 | 3.3 ± 1.1 | 12.6 ± 2.9 | 22.1 ± 2.3 |
| Sample 5 | Sample E | 1.0 ± 0.23 | 3.2 ± 1.0 | 12.1 ± 2.3 | 22.9 ± 4.8 |
| | Sample e | 1.2 ± 0.28 | 3.7 ± 1.2 | 13.9 ± 3.9 | 19.9 ± 3.6 |
| Sample 6 | Sample F | 0.37 ± 0.14 | 1.1 ± 0.6 | 4.2 ± 1.6 | 66.1 ± 4.9 |
| | Sample f | 0.42 ± 0.13 | 1.3 ± 0.7 | 4.9 ± 1.5 | 57.5 ± 5.7 |
| Sample 7 | Sample G | 0.57 ± 0.21 | 1.7 ± 0.6 | 6.5 ± 2.1 | 42.7 ± 4.3 |
| | Sample g | 0.65 ± 0.25 | 2.0 ± 0.9 | 7.5 ± 2.9 | 37.2 ± 5.2 |
| Sample 8 | Sample H | 0.91 ± 0.34 | 3.5 ± 0.8 | 10.3 ± 2.9 | 26.9 ± 3.1 |
| | Sample h | 0.98 ± 0.32 | 3.8 ± 1.3 | 11.8 ± 3.1 | 23.4 ± 2.8 |
| Sample 9 | Sample I | 0.5 ± 0.26 | 1.5 ± 0.5 | 5.9 ± 2.0 | 47.7 ± 4.8 |
| | Sample i | 0.59 ± 0.21 | 1.8 ± 0.8 | 6.7 ± 2.4 | 41.5 ± 5.1 |

After receiving UV radiation, the mice applied with the samples A-I (i.e., the bee venom compositions with effects of protecting and beautifying lips made according to embodiments 1-9) had lower average values of ear index, skin index and epidermis thickness than those of the mice applied with the samples a-i (i.e., the control groups vs. samples A-I, wherein no bee venom, moisturizing ingredient or repairing ingredient contained in the control groups), and the numbers of the fibroblast in the dermal issue were higher than those of the mice applied with the samples a-i.

The test results showed that the bee venom composition with effects of protecting and beautifying lips could effectively restrain thickening of the damaged epidermis caused by UV radiation, inhibit epidermal keratinization, reduce inflammation and induce generation of the fibroblast. The bee venom composition with effects of protecting and beautifying lips according to the present invention can protect the skin from UV damage and improve the skin's shielding function and self-protecting function. It had multi-functions such as inflammation diminishing and repairing.

Embodiment 11

Lip-beautifying evaluation was applied with the following samples:

The percentage in this embodiment referred to mass concentration.

In this embodiment, the wasp venom and the honeybee venom were prepared according to the method in embodiment 3:

Cosmetic matrixes: 3% of fatty alcohol-polyoxyethylene ether, 9% of $C_{12}$-$C_{15}$ alkyl benzoate, 2% of dicaprylyl carbonate, 0.8% of microcrystalline wax, 0.2% of azone/PEG-40 hydrogenated castor oil, 0.5% of xanthan gum, 0.8% of NaCl, 5% of 1,3-butanediol, 4% of propylene glycol, 0.1% of EDTA-2Na, 0.5% of butylparaben, 0.2% of green tea essence, and the balance being deionized water.

Cosmetic composition containing crude bee venom (i.e., sample A, wherein the mass content of the crude bee venom was 2%):

A1: 2% of crude wasp venom, 98% of cosmetic matrix;
A2: 0.5% of crude wasp venom, 1.5% of crude honeybee venom, and 98% of cosmetic matrix.

Cosmetic composition containing bee venom (i.e., sample B, wherein the mass content of the bee venom was 2%):

B1: 2% of wasp venom, 98% of cosmetic matrix;
B2: 0.5% of wasp venom, 1.5% of honeybee venom, and 98% of cosmetic matrix;

Cosmetic composition containing moisturizing ingredients (i.e., sample C, wherein the mass content of the moisturizing ingredients was 2%):

C1: 1% of honey, 1% of hyaluronic acid and 98% of cosmetic matrix;
C2: 0.1% of allantoin, 1.4% of aloe extract, 0.5% of algae extract and 98% of cosmetic matrix.

Cosmetic composition containing bee venom and moisturizing ingredients (i.e., sample D, wherein the total mass content of the bee venom and the moisturizing ingredients was 2%):

D1: 1% of wasp venom, 0.5% of honey, 0.5% of hyaluronic acid and 98% of cosmetic matrix;
D2: 0.5% of honeybee venom, 0.5% of wasp venom, 0.1% of allantoin. 0.5% of aloe extract, 0.4% of algae extract and 98% of cosmetic matrix.

Cosmetic composition containing repairing ingredients (i.e., sample E, wherein the mass content of the repairing ingredients was 2%):

E1: 1% of Vitamin E acetate, 1% of Vitamin C magnesium ascorbyl phosphate and 98% of cosmetic matrix;
E2: 0.5% of coenzyme $Q_{10}$, 1% of olive oil, 0.5% of grape seed oil and 98% of cosmetic matrix.

Cosmetic composition containing bee venom and repairing ingredients (i.e., sample F, wherein the total mass content of the bee venom and the repairing ingredients was 2%):

F1: 0.5% of wasp venom, 1% of Vitamin E acetate, 0.5% of Vitamin C magnesium ascorbyl phosphate and 98% of cosmetic matrix;
F2: 0.4% of honeybee venom, 0.4% of wasp venom, 0.2% of coenzyme $Q_{10}$, 0.5% of olive oil, 0.5% of grape seed oil and 98% of cosmetic matrix.

39 healthy volunteers were selected including 11 males and 28 females, aged 37-42, with an average age of 40.3. The volunteers had no serious systemic diseases, immunodeficiency or autoimmune diseases, were not allergic to cosmetics, and did not suffer facial acute inflammation, used no glucocorticoid or immunosuppressor, participated in no other clinic tests, and not coated with any other external preparations. They were randomly divided into 13 groups, namely the group of cosmetic matrix, the group of cosmetic composition containing crude bee venom (samples A1-A2), the group of cosmetic composition containing bee venom (samples B1-B2), the group of cosmetic composition containing moisturizing ingredients (samples C1-C2), the group of cosmetic composition containing bee venom and moisturizing ingredients (samples D1-D2), the group of cosmetic composition containing repairing ingredients (samples E1-E2), and the group of cosmetic composition containing bee venom and repairing ingredients (samples F1-F2). Three persons were included in each group.

The samples were respectively applied onto the lip skin of the volunteers of each group. After 4 h, lip skin improving effects were evaluated.

The skin hydration (%) in the cuticle of the lip was measured using Corneometer® CM 825. Lip skin elasticity was measured using Cutometer® dual MPA 580 (the negative pressure was kept at 450 mbar during measuring). The biological elasticity was represented by the ratio of retraction Ur (i.e., the recovery value of the skin after the negative pressure was removed for 0.1 s) to the total deformation Uf of the skin. The closer the value approached 1, the better the skin elasticity was.

The skin wrinkles of the lips were measured using Skin-Visiometer® SV 600 (a skin wrinkle mold in accordance with the tested position was build using silicon mold. The grade classification and statistic treatment were carried out according to the depth of the skin wrinkles by a computer). The average roughness R3 of the skin was calculated before and after the use of the samples (i.e., taking the arithmetic average of values R1 obtained through measuring five different segments with identical length, wherein R1 represented the distance between the peak value and the valley value in a certain length, μm). The result was represented by ΔR3 (i.e., the difference of the average skin roughness between before and after using the samples). The higher the value was, the better the effect of wrinkles relieving was.

The same lip site was photographed using DIGIMIC800 skin image analyzer to measure the change of thickness (μm) before and after the samples applied to the lips. The change of lip color was measured using the Spectrophotometer CM-2600d (L* value represented the lightness of skin. The higher the L* was, the lighter the skin was. The difference value ΔL* of the skin lightness before and after using the samples can represent the change in the skin color).

The test results were shown in Table 2, wherein the sample A represented the average value of the groups of samples A1, A2; sample B represented the average value of the groups of samples B1, B2; sample C represented the average value of the groups of samples C1, C2; sample D represented the average value of the groups of samples D1, D2; sample E represented the average value of samples E1, E2; and sample F represented the average value of the groups of samples F1, F2.

TABLE 2

Effects of different samples on the improvement of lip skin

| Group | side effect | skin hydration (%) | biological elasticity (i.e., Ur/Uf) | Change in average roughness of the skin (ΔR3, μm) | Change in thickness of lips (μm) | Change in lip lightness(ΔL*) |
|---|---|---|---|---|---|---|
| Cosmetic matrix | Local redness, one person had slight pruritus | 15.1 ± 1.2 | 0.34 ± 0.06 | 13.9 ± 0.6 | 20.8 ± 1.2 | 0.5 ± 0.3 |

TABLE 2-continued

Effects of different samples on the improvement of lip skin

| Group | side effect | skin hydration (%) | biological elasticity (i.e., Ur/Uf) | Change in average roughness of the skin ($\Delta R3$, μm) | Change in thickness of lips (μm) | Change in lip lightness($\Delta L^*$) |
|---|---|---|---|---|---|---|
| Sample A (i.e., the cosmetic composition containing crude bee venom) | Local redness and stabbing pain, two persons felt hot | 31.1 ± 1.3 | 0.59 ± 0.07 | 29.4 ± 0.7 | 280.2 ± 1.7 | 1.4 ± 1.0 |
| Sample B (i.e., the cosmetic composition containing bee venom) | No obvious side effect | 36.5 ± 1.9 | 0.75 ± 0.09 | 31.1 ± 1.6 | 310.7 ± 1.6 | 1.9 ± 0.9 |
| Sample C (i.e., the cosmetic composition containing moisturizing ingredients) | No obvious side effect | 30.8 ± 1.5 | 0.57 ± 0.06 | 23.2 ± 1.0 | 30.8 ± 1.1 | 0.8 ± 1.2 |
| Sample D (i.e., the cosmetic composition containing bee venom and moisturizing ingredients) | No obvious side effect | 41.1 ± 1.7 | 0.82 ± 0.05 | 36.4 ± 1.5 | 360.2 ± 2.7 | 2.2 ± 1.1 |
| Sample E (i.e., the cosmetic composition containing repairing ingredients) | No obvious side effect | 23.8 ± 1.4 | 0.70 ± 0.08 | 27.5 ± 0.8 | 30.9 ± 1.2 | 1.2 ± 0.8 |
| Sample F (i.e., the cosmetic composition containing bee venom and repairing ingredients) | No obvious side effect | 37.3 ± 1.1 | 0.91 ± 0.09 | 36.8 ± 0.7 | 350.1 ± 2.8 | 2.5 ± 1.1 |

Compared with the cosmetic matrix, samples A-F had obvious effects of improving the hydration, elasticity, tension, thickness and lightness of the lip skin, and eliminating the dryness, roughness and wrinkles. This showed that the cosmetic composition containing bee venom, the cosmetic composition containing bee venom and moisturizing ingredients, and the cosmetic composition containing bee venom and repairing ingredients all had obvious effects of protecting and beautifying lips.

Because the allergens in the crude bee venom had been removed, compared with the cosmetic composition containing crude bee venom (i.e., sample A), the cosmetic composition containing bee venom (i.e., sample B) had no obvious irritation to the lip skin and could relieve the allergy of the lip care product matrix to the skin. Because the beautifying and skin-caring components had been enriched in the bee venom, the effects of the cosmetic composition containing bee venom (i.e., sample B) on improvements of the hydration, elasticity, tension, thickness and lightness of the lip skin, and elimination of dryness, roughness and wrinkles, were better than the cosmetic composition containing crude bee venom (i.e., sample A).

Compared with the cosmetic composition containing bee venom (i.e., sample B) and the cosmetic composition containing moisturizing ingredients (i.e., sample C), the effects of the cosmetic composition containing bee venom and moisturizing ingredients (i.e., sample D) on the improvement of lip hydration, elasticity, tension and thickness, and the elimination of dryness and roughness, were enhanced obviously. This showed that the moisturizing ingredients and the bee venom in the present invention had a synergistic effect, which can obviously enhance the effects of the bee venom composition provide herein on lip protecting and beautifying, such as moistening, nourishing, plumping and wrinkle repairing.

Compared with the cosmetic composition containing bee venom (i.e., sample B) and the cosmetic composition containing repairing ingredients (i.e., sample E), the effects of the cosmetic composition containing bee venom and repairing ingredients (i.e., sample F) on the improvement of elasticity, tension, thickness and lightness, and the elimination of roughness and wrinkles, were enhanced obviously. This showed that the repairing ingredients and the bee venom in the present invention had a positive synergistic effect which could obviously improve the bee venom composition's lip protecting and beautifying effects such as repairing, sun blocking, lip plumping, lip brightening, and lip wrinkles eliminating.

In a word, the bee venom composition with effects of protecting and beautifying lips according to the present invention can be quickly absorbed by skin to supply histocyte with nutrient substances, improve microcirculation, prevent chap and cell aging. In addition, it can also comprehensively enhance the self-protection capability of the skin. After applied to lips, the chapped lips can be healed within 3 days. Meanwhile, the bee venom composition with effects of protecting and beautifying lips according to the present invention can plump and shape the lips to make it sexy, adjust the skin color, reduce fine lines, and make the lip skin exquisite, sanguine, shiny, charming and beautiful.

In addition, the bee venom composition with effects of protecting and beautifying lips according to the present invention can be also added with colorants as required to meet the demands of various populations.

The embodiments above are preferable embodiments of the present invention. However, methods for implementing the present invention shall not be limited by the embodiments as above. Any change, modification, substitution, combination and simplification made without deviating from the spirit and principle of the present invention shall be regarded as an equivalent substitute mode and shall fall within the protective scope of the present invention.

What is claimed is:

1. A composition, comprising the ingredients below in percentages by weight:
   2% honeybee venom, 13% aloe extract, 1% algae extract, 0.1% xanthan gum, 2% glycerin, 5% propylene glycol, 0.2% triethanolamine and 1% hyaluronic acid;
   wherein said composition provides for plumping lips and protecting lips from UV radiation.

2. The composition according to claim 1, wherein the honeybee venom is prepared by the following steps: dissolving crude honeybee venom with water before performing ultrafiltration using an ultrafiltration membrane with a MWCO (Molecular Weight Cutoff) of 10,000 Da; and freeze-drying a resulting filtrate to obtain the honeybee venom.

3. The composition according to claim 2, wherein the honeybee venom is prepared by the following steps: dissolving crude honeybee venom with a volume of water 10-30 times the volume of the crude honeybee venom, followed by performing centrifugation at 5,000-10,000 g for 10-30 min; performing ultrafiltration of the resulting supernatant using an ultrafiltration membrane with a MWCO of 10,000 Da; and freeze-drying a resulting filtrate to obtain the honeybee venom.

4. The composition according to claim 1, wherein the composition is a lip balm, lip cream, lip gloss, lip stain or lip mask.

5. A lip care product comprising the composition of claim 1.

* * * * *